US00PP36069P2

(12) United States Plant Patent
Hansen

(10) Patent No.: US PP36,069 P2
(45) Date of Patent: Aug. 13, 2024

(54) ***XMANGAVE* PLANT NAMED 'Aztec Treasure'**

(50) Latin Name: **x *Mangave***
Varietal Denomination: Aztec Treasure

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 18/445,761

(22) Filed: Jan. 22, 2024

(51) Int. Cl.
*A01H 5/12* (2018.01)
*A01H 6/00* (2018.01)

(52) U.S. Cl.
USPC ..... Plt./373

(58) Field of Classification Search
USPC ..... Plt./373
See application file for complete search history.

(56) References Cited

U.S. PATENT DOCUMENTS

PP30,650 P2 * 7/2019 Hansen ..... A01H 5/12
Plt./373

* cited by examiner

*Primary Examiner* — Karen M Redden

(57) ABSTRACT

A new and unique x *Mangave* plant named 'Aztec Treasure' characterized by a large mound of large, broad, fleshy, glaucous-green foliage with creamy-yellow margins that is outwardly and slightly arching with age. The foliage has large greyed-purple to purplish-red spots that intensify from with greater ultraviolet light exposure. The leaves have fine teeth that are flexible when young and become slightly firm when mature. The new plant is suitable for the garden or as a potted plant in the garden or home.

1 Drawing Sheet

Botanical classification: hybrid; *Manfreda* times *Agave*, known as x *Mangave*.

Variety denomination: 'Aztec Treasure'.

STATEMENT REGARDING PRIOR DISCLOSURES UNDER 37 CFR 1.77(b)(6)

No plants of x *Mangave* 'Aztec Treasure' have been sold, in this country or anywhere in the world, nor has any disclosure of the new plant been made, more than one year prior the filing date of this application, and such sale or disclosure within one year was either derived directly or indirectly from the inventor.

BACKGROUND OF THE INVENTION

The present invention relates to the new and distinct x *Mangave* hybrid plant, x *Mangave* 'Aztec Treasure' was discovered by the inventor at a wholesale perennial nursery in Zeeland, Michigan, USA as a whole plant mutation of x *Mangave* 'Aztec King' U.S. Plant Pat. No. 32,151. The mutation was found on Mar. 9, 2021, and identified by the breeder code 21-sp-MANG-1028 through the evaluation trials at the same nursery. The new plant has been successfully asexually propagated initially by removal of basal offsets since 2024 at the same nursery in Zeeland, Michigan, and by sterile shoot-tip tissue culture. Both methods of asexual propagation systems have been found to produce stable and identical plants that maintain all the unique characteristics of the original plant.

BRIEF SUMMARY OF THE INVENTION

'Aztec Treasure' differs from its parents as well as all other *Manfreda, Agave*, and x *Mangave* known to the applicant. The parent has similar habit and foliage characteristics but lacks the marginal light yellow chimeral variegation.

The nearest comparison plants are: 'Life on Mars' U.S. Plant Pat. No. 32,939, 'Falling Waters' U.S. Plant Pat. No. 30,650, and 'Kaleidoscope' U.S. Plant Pat. No. 28,614.

'Life on Mars' has a larger more horizontal and less arching habit, larger foliage that is slightly more cupped, with larger marginal teeth, and the leaf center is more reddish and less glaucous. 'Falling Waters' is a smaller plant with leaves that are more arching, with less greyed-purple spotting, and without a creamy-yellow margin. 'Kaleidoscope' has a more arching habit with narrower foliage that is not as thick, the margin tends to be slightly deeper yellowish, and the center is less glaucous.

The new plant, 'Aztec Treasure', is unique from the above cultivars, and all *Agave*, x *Mangave*, and *Manfreda* known to the inventor by the following combined traits:

1. Large mound of large, lanceolate, broad, fleshy foliage;
2. Glaucous bluish-green foliage is variegated with creamy-yellow margins;
3. Foliage has large greyed-purple to purplish-red spots that become more pronounced and overlapping in strong ultraviolet light;
4. Leaf margins finely toothed initially flexible becoming firm with maturity;
5. Moderate growth rate.
6. Foliage outwardly or arching with age.

BRIEF DESCRIPTION OF THE DRAWING

The photograph of x *Mangave* 'Aztec Treasure' demonstrates the overall appearance of the new plant including the unique traits of a three-year-old plant grown in a partially shaded greenhouse with supplemental water and fertilizer as needed. The colors are as accurate as reasonably possible with color reproductions. Ambient light spectrum, temperature, source, and direction may cause the appearance of minor variations in color.

DETAILED BOTANICAL DESCRIPTION

Figure 1:
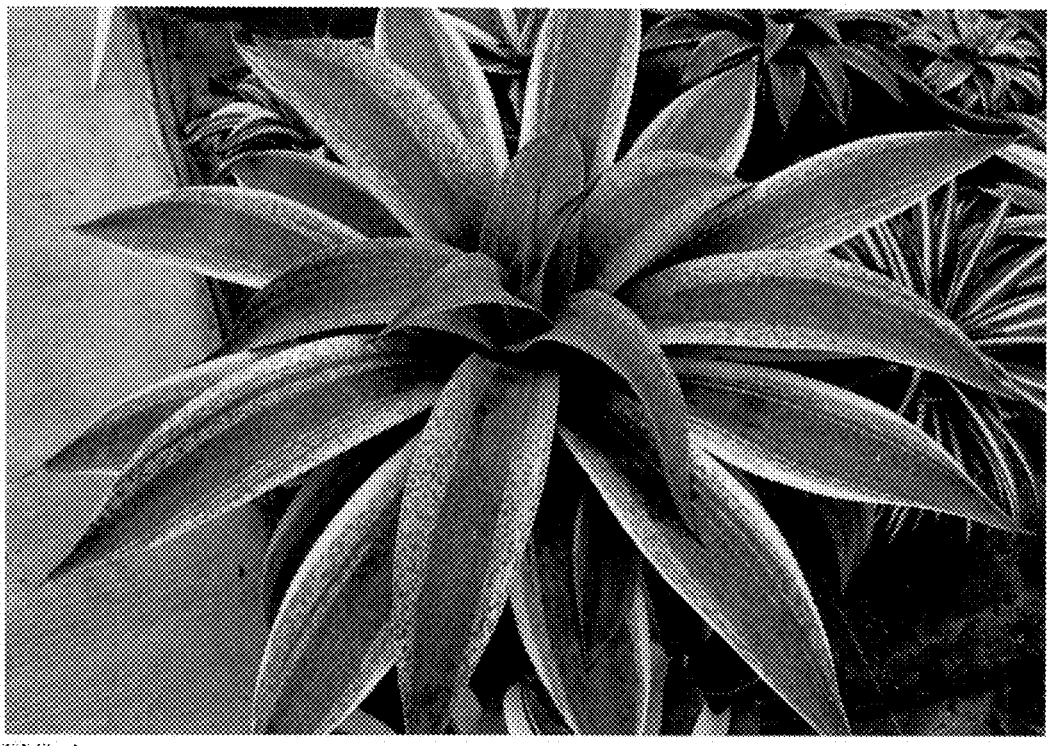
FIG. 1 shows the habit of the container-grown plant in a greenhouse.
Figure 2:
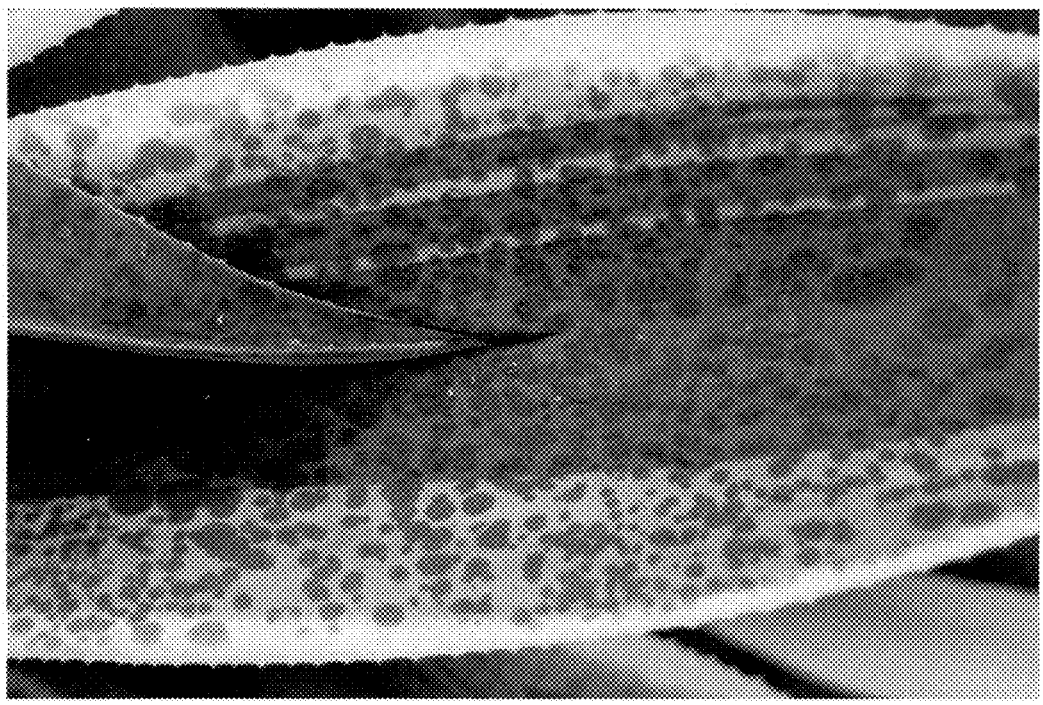
FIG. 2 shows a close-up of young foliage above a mature leaf.

The following descriptions and color references are based on the 2015 edition of The Royal Horticultural Society Colour Chart except where common dictionary terms are used. The new plant, x *Mangave* 'Aztec Treasure', has not been observed under all possible environments. The phenotype may vary slightly with different environmental conditions, such as temperature, light, fertility, moisture and maturity levels, but without any change in the genotype. The following observations and size descriptions are of a three-year-old plant in a commercial wholesale greenhouse in Zeeland, Michigan with supplemental water and fertilizer as needed.

*Parentage*.—a whole plant mutation of 'Aztec King'.

*Propagation*.—by sterile shoot-tip tissue culture.

*Time to initiate roots from tissue culture*.—about 21 to 28 days.

*Growth rate*.—moderate.

*Crop time*.—about 20 to 24 weeks to finish in a 3.8-liter container from a 35 mm tissue culture growing at about 21° C.

*Rooting habit*.—fleshy, lightly branching, with roots up to 40 cm long; color nearest RHS 158C.

*Plant shape and habit*.—succulent herbaceous perennial with basal rosettes of about 42 leaves radially emerging outwardly from central stem and arching distally, producing a radially-symmetrical, rounded mound.

*Plant size*.—foliage height about 32 cm tall from the soil line to the top of the leaves and about 100 cm wide at the widest point slightly below the soil line in a container.

*Foliage description*.—lanceolate; simple; sessile; sarcous; bi-laterally symmetrical; apex acute with terminal spine; terminal spine to about 12.0 mm long; base truncate; longitudinally conduplicate, especially young leaves; margins developing a creamy-yellow variegation in maturity, finely dentate with teeth slightly curved toward stem; glaucous waxy bloom abaxial and adaxial without trichomes; with adaxial spots about 10 mm long to 5 mm wide frequently touching or overlapping, and abaxial spots to 5 mm long and 4 mm wide.

*Teeth*.—initially flexible, becoming hard and sharp with age; about 1.5 mm long and about 2 mm wide at base; average about 5 mm apart in middle of mature leaves and decreasing distally and proximally.

*Leaf size*.—to about 50.5 cm long, about 11.3 cm wide toward the middle, and 1 cm thick near the base; average about 46 cm long, 10 cm wide, and 8 mm thick.

*Variegation dimensions*.—adaxial margin broadening with maturity to about 1.2 cm wide, center between 4.5 cm to 6.5 cm wide, intermediate region to about 2.2 cm wide; abaxial margin to 14 mm wide, center between 7 cm and 9 cm, intermediate region to about 4 mm when visible.

*Mucro or terminal spine*.—stiff, sharp; to about 17 mm long and 2 mm wide at base.

*Foliage fragrance*.—none observed.

*Leaf number*.—about 42 per plant.

*Leaf Blade Color*.—Adaxial (young expanding): margin nearest RHS N138C with spots between RHS N187A to RHS N186B, center between RHS N138A and RHS 189A with spots between RHS N187A to RHS N186B, intermediate region indistinguishable; Abaxial (young expanding): margin, center, and intermediate region indistinguishable with all regions nearest RHS N138B with spots nearest RHS N187B to RHS 187B; Adaxial (mature): margin between RHS 11D and RHS 19D, with spots between RHS 186B and RHS 186C, center between RHS N138A and RHS 189A with spots between RHS N187A to RHS N186B, intermediate region nearest RHS 191D with spots nearest RHS 186B and random longitudinal streaks of between RHS N138A and RHS 189A; Abaxial (mature): margin nearest RHS 11D and spots to nearest RHS 186D, center between RHS N138A and RHS 189B with spots nearest RHS N187C, intermediate region when distinguishable between RHS N138D and RHS 155C with spots of nearest RHS 186C and occasional random longitudinal streaks of between RHS N138A and RHS 189B; Teeth: beginning nearest RHS 157D and maturing to between RHS 11D and RHS 19D; Mucro or terminal spine: on young emerging and mature leaves nearest RHS 200A;

*Petiole*.—leaves sessile.

*Veins*.—parallel; not distinct abaxial or adaxial.

*Flower description*.—not yet observed to date. Fruit and seed not observed to date;

*Disease resistance*.—*x Mangave* 'Aztec Treasure' has not been observed to be resistant to diseases beyond that which is normal for x *Mangave, Agave*, or *Manfreda*. The new plant is xeromorphic and survives well with minimal water once established. The new plant is estimated to be cold-hardy at least from USDA zone 9. The full extent of winter hardiness has not been tested.

It is claimed:

1. A new and distinct cultivar of ornamental x *Mangave* plant named 'Aztec Treasure' as herein described and illustrated.

* * * * *